United States Patent [19]

Changaramponnath et al.

[11] Patent Number: 5,387,702
[45] Date of Patent: Feb. 7, 1995

[54] PROCESS FOR THE PREPARATION OF CABOFURAN

[75] Inventors: Gopinathan Changaramponnath; Gopinathan Sarada; Mitra R. Baran; Ratnasamy Paul, all of Pune, India

[73] Assignee: Council of Scientific And Industrial Research, New Delhi, India

[21] Appl. No.: 128,152

[22] Filed: Sep. 29, 1993

[51] Int. Cl.6 .......................................... C07D 307/86
[52] U.S. Cl. .................................... 549/470; 549/462
[58] Field of Search ................................ 549/462, 470

[56] References Cited

FOREIGN PATENT DOCUMENTS 60-100569  7/1985  Japan .

Primary Examiner—Bernard Dentz
Attorney, Agent, or Firm—Michael D. Bednarek

[57] ABSTRACT

A process for the preparation of carbofuran which is used as an insecticide. Carbofuran is the N-methylcarbamate of 7-benzofuranol. Carbofuran is prepared by reacting catechol with beta methallyl halide or the alcohol in the presence of a catalyst composite containing a heteropoly acid and reacting the 7-hydroxy 2, 3, dihydro-2, 2, dimethyl benzofuranol thus obtained with methyl isocyanate or with phosgene and methylamine to obtain carbofuran.

12 Claims, No Drawings

PROCESS FOR THE PREPARATION OF CABOFURAN

The invention relates to an improved process for the preparation of carbofuran. The present invention involves a single step process for the preparation of 7-hydroxy-2, 3, dihydro 2, 2 dimethylbenzofuran referred to as 7-benzofuranol which is further converted into carbofuran. The single step process of preparing 7-benzofuranol consists of reacting catechol with methallyl halide or the alcohol in the presence of a solid catalyst composite material consisting of a heteropoly acid, which process has been made the subject matter of our copending Indian Patent Application No. 368/Del/93.

Carbofuran is a well known carbamate insecticide used extensively worldwide. Carbofuran is the N-methylcarbamate of 7-benzofuranol. In the art, carbofuran is manufactured by the reaction of 7-benzofuranol with methyl isocynate (MIC) in a non-polar solvent like benzene or toluene in the presence of a basic catalyst like trimethylamine. Non-MIC routes to prepare carbofuran are also known. U.S. Pat. Nos. 4086246 and 4272441 describe the preparation of carbofuran involving reaction of benzofuranol sequentially with phosgene and methylamine. 7-benzofuranol is the intermediate in most of the known methods of preparation of carbofuran.

Several methods for the preparation of 7-benzofuranol are known in the prior art. U.S. Pat. No. 4463184 describes a process wherein 1, 2-cyclohexanedione is first reacted with betamethallyl alcohol or its halide in the presence of alkylation catalyst to form 2-beta methallyloxy-2-cyclohexen-1-one to a temperature sufficient to cause rearrangement and aromatisation to 7-benzofuranol.

In commercial practice, 7-benzofuranol is also prepared from catechol as a starting material. The preparation involves three distinct chemical process steps. In the first step, catechol is reacted with methallyl chloride to form the mono- methallyl ether of catechol. High selectivity to the monoether in this step is of prime importance since any diether formed in this step as a by-product is difficult to remove. It also contributes to low overall yield of the final product and expensive effluent disposal problems. In the second step, the monoether is thermally rearranged to 3-methallyl catechol. In the third step, the latter is cyclised using an acid or Lewis acid catalyst to obtain 7-benzofuranol. It is also known in the prior art to combine the second and third steps of rearrangement and cyclisation by heating the monoether in the presence of an acid or Lewis acid catalyst to obtain 7-benzofuranol.

Hence, in the prior art, at least two distinct process steps are required in the preparation of 7-benzofuranol from catechol involving (1) preparation of the monomethallyl ether of catechol and (2) rearrangement and cyclisation of the monoether to 7-benzofuranol. Several methods are known, in the prior art, to carry out each of these two steps. Thus, for the first step of etherification U.S. Pat. No. 3747171, describes the reaction of catechol with methallyl chloride in acetone as solvent and in the presence of sodium carbonate as an acid binding agent with potassium iodide as catalyst. U.S. Pat. No. 3927118 describes the use of a highly polar aprotic solvent like dimethyl sulphoxide with sodium hydroxide for the reaction of catechol with methallyl chloride and claims the selective formation of the monoether. U.S. Pat. 4514086 describes the use of the sodium salt of catechol with methallyl chloride in a non-polar solvent like toluene and using tertiary amines as sequestering agents. U.S. Pat. No. 4250333 describes a process for the selective monoetherification of catechol wherein catechol and methallyl chloride are reacted in a 2-phase system of chlorobenzene/water in presence of a mixture of sodium carbonate and sodium hydroxide and using a phase transfer catalyst like tetrabutyl ammonium bromide. European Patent 92102, in another modification, claims low diether formation wherein decalin is used as a solvent with a mixture of sodium carbonate and sodium hydroxide in water and tetrabutyl ammonium bromide as a phase transfer catalyst.

It is evident from the foregoing references to prior art, that considerable research effort has gone into attempts to increase selectivity for monoether formation in the reaction of catechol with methallyl chloride. However, in all these processes 10 to 20 percent of diether is invariably formed which, as mentioned hereinbefore, lowers the efficiency of the overall process to produce 7-benzofuranol.

For the second and third steps involved in the preparation of 7-benzofuranol, namely the rearrangement and cyclisation of the mono methallyl ether of catechol to 7 benzofuranol, U.S. Pat. Nos. 4524751 and 4580654 described processes involving heating the methallyl ether in an organic solvent with aluminum chloride as a Lewis acid catalyst. European Patent 92102 describes a process wherein an insoluble acid catalyst is used in an organic solvent. Euorpean Patent 115837 describes the use of metal carboxylates as catalysts in an organic solvent for converting mono methallyl ether of catechol to 7-benzofuranol.

In all the prior art processes for converting mono methallyl ether of catechol to 7-benzofuranol, because of the invariable presence of the diether as an impurity in the monoether, the crude 7-benzofuranol obtained is quite impure and requires purification by careful fractional distillation of high boiling constituents with consequent loss in yield of pure product and serious byproduct and effluent disposal problems.

In view of the above limitations of the prior art processes for the manufacture of 7-benzofuranol, the intermediate for carbofuran, it was found desirable during the course of the investigation leading to the present invention to develop a process which can produce the 7-benzofuranol from catechol and methallyl halide or alcohol in a single process step and in high selectivity utilising a catalyst with a long stable active life and forming very little other undesired products such as the diethers.

It is an object or the present invention to provide an improved process, particularly , a process capable or operating in the continuous mode and which uses preferably, a solid catalyst with a long life.

Accordingly, the present invention provides an improved process for the preparation of carbofuran which comprises reacting catechol with beta methallyl halide or alcohol in the presence of a solid catalyst composite containing a heterpoly acid and reacting the 7- hydroxy 2, 3 dihydro 2,2, dimethyl benzofuranol formed with methyl isocyanate or with phosgene and methyl amine.

In a preferred embodiment of the invention, the reaction of the catechol with the beta methallyl halide or the alcohol may be carried out at a temperature in the range of 100° to 400° C. The ratio of catechol with the methallyl halide or alcohol may be in the range of 0.5 to 20 moles, preferably around 10 moles. The weight hourly velocity of the feed may be in the range of 0.1 to 10 gm/gm, preferably 0.3 to 2.0. The heteropoly acid may be selected from silicotungstic acid, phosphotungstic acid, silicomolybdic acid or the mixtures thereof. The concentration of the catalyst employed may range form 5 to 80% by weight, preferably between 10 to 50%.

In one aspect of the present invention, the process involves the use of a solid catalytic composite containing heteropoly acid for the selective esterification of the one of the two hydroxyl groups of the catechol with the methallyl halide or the alcohol which have a structure comprising of a central tetrahedron constituted of, for example, $SiO_4$ or $PO_4$ units surrendered by twelve $MO_6$ octahedra wherein M=Mo or W. The methallyl halide used may be selected from chloride or bromide.

In another embodiment of the present invention, the heteropoly acid may be combined with a binder to constitute the final catalyst composite material. Such an operation imparts to the catalyst a few desirable properties such as good mechanical strength, large and active surface, ease of handling, lower and optimal utilization of the heteropoly acid. Examples of such binders are silica, alumina, thoria, silica alumina, clays, kieselguhr etc. A particularly preferred binder is silica, Indian Patent No. 164459 and copending Indian Application No.1113/Del/87 describe a process for the preparation of a light olefin and kerosene respectively, using heteropoly acid based solid catalyst composite material.

Catalysts used in the prior art for the esterification of catechol yield significant amounts of diethers. One novel feature of the process of the present invention is that the heteropoly acid catalyst used herein does not lead to the formation of the diethers, the concentration of the 7-benzofuranol amongst the ethers of catechol exceeds 95%. The use of the catalyst composite material containing the heteropoly acid which is more fully described in Indian Patent No. 164459 and copending Indian Application No. 1113/Del/87 when employed in the process of the present invention leads to significant advantages in the manufacture of 7-benzofuranol.

Further embodiment of the present invention provides that the catalyst composite material is prepared by impregnating an aqueous solution of a heteropoly acid on an inert binder to obtain an uniform impregnation of the catalytically active material, the heteropoly acid, on the high surface, inert binder followed by removal of the water by drying at a temperature not exceeding 400° C.

In another embodiment of the present invention, the inert binder can be of any convenient physical forms like granules, extrudates, tablets, rings etc., which are known to those skill in the art.

In yet another embodiment of the invention, the process of the invention can be performed with a heteropoly acid in the vapor phase.

In a preferred embodiment of the present invention, the catechol is reacted with methallyl halide or the alcohol at temperatures between 100° to 400° C. in presence of a solid catalyst comprising of a heteropoly acid combined with an inert support in a flow reactor. The ratio the methallyl alcohol or halide to the catechol could be varied from 0.5 to 20 moles (preferably around 10) and the weight hourly space velocity of the feed, comprising of catechol and methallyl alcohol or halide, between 0.1 to 10 gm/gm (preferably 0.3 to 2). The concentration of the heteropoly acid in the catalyst composite could be varied between 5 to 80% by weight (preferably between 10 to 30 %. The 7-benzofuranol can be separated from the products of the reaction by fractional distillation.

The invention is described with reference to the Examples given below which are given by way of illustration only and therefore should not be construed to limit the scope of the present invention.

EXAMPLE 1.

(a) Preparation of the catalyst

Silica gel prepared from sodium silicate and dilute. Sulfuric acid mesh size ranging from 5 to 15 was used as the support. Phosphotungstic acid (10 g) was dissolved in water (25ml) and the solution was mixed with silica gel (110 g.) The slurry was stirred to get an uniform impregnation dried in air at 200° to 250° C. in a silica dish for one hour, then at 400° C. for three hours and finally cooled to room temperature in a desiccator. This catalyst was used for the preparation of 7-benzofuranol.

(b) Preparation of 7-benzofuranol

The experiment was carried out in a downward flow glass reactor which was kept in a furnace. In the middle of the reactor, the catalyst (11 g) made as explained above was kept and heated to a temperature in the range of 500° to 520° C. in a current of air. A solution of catechol (11 g) in methallyl alcohol (72 g) was fed at a rate of 8 ml/hr. The products formed were condensed in a water cooled receiver, weighed and analyzed by gas chromatography using SE-30 column with temperature from 70° to 180° C. Pure standard substances were used for calibration. The products were also analyzed and identified by GC mass spectroscopy techniques. The conversion of catechol was found to be 55% and selectivity to 7-benzofuranol 95%.

Preparation of carbofuran

The 7benzofuranol obtained by the process described above was dissolved in benzene. To this solution, methyl isocyanate and triethyl amine were added. The whole mixture was refluxed at 80° C. for 3 hrs. During refluxing the 7 benzofuranol was converted to carbofuran. The reaction mixture was dried. The yield of carbofuran was 95%.

EXAMPLE 2

A mixture containing catechol (11 g), beta methallyl chloride (91 g) and tetrahydrofuran (36 g) (solvent) was fed in to a reactor at a rate of 10 ml/hr at a temperature in the range of 210° C. to 230°C. using the catalyst phosphotungstic acid. The procedure explained in Example 1 was followed. The conversion of catechol as found to be 40% and the selectivity of 7-benzofuranol 50%.

The products containing 7-benzofuranol obtained as above were dissolved in benzene (solvent, 80 ml) and methyl isocyanate (3 g) and triethyl amine (catalyst 0.3 g) were added to the solution. The whole mixture was refluxed to 80° C. for 4 hrs. During this period 7-benzofuranol was converted into carbofuran. Pure carbofuran was obtained from the mixture by filtration and drying. Yield of carbofuran was 95%.

EXAMPLE 3

A mixture containing catechol (22 g), methallyl alcohol (72 g) and a solvent (acetonitrile; 44g) was fed over a catalyst (11.5 g) containing silicotungstic acid (1.5 g)

and silica (10 g) at a rate of 10 ml per hr. The per pass conversion of catechol was 4% and selectivity to 7-benzofuranol 95%. The products containing 7-benzofuranol obtained as above were dissolved in benzene (solvent, 60 ml) and methyl isocyanate (6.1 g) and triethyl amine (catalyst, 0.5 g) were added to this solution. The whole mixture was refluxed to 80° C. for 5 hrs. During this period, 7-benzofuranol was converted into carbofuran. Pure carbofuran was obtained from the mixture by filtration and drying. Yield of carbofuran was 90%.

EXAMPLE 4

A mixture containing catechol (11 g), beta-methallyl chloride (91 g) and a solvent (chlorobenzene; 110 g) was fed over a catalyst (12 g) containing phosphomolybdic acid (2 g) and silica (10 g) at a rate of 6 ml/hr. The per pass conversion of catechol was 50% and selectivity to 7-benzofuranol 96%. The mixture containing 7-benzofuranol obtained as above was mixed with benzene (solvent, 70 ml). Methyl isocyanate (3 g) and triethyl amine (catalyst, 0.25 g) were added to this solution and refluxed for 4 hrs. During the refluxing, the benzofuranol got converted into carbofuran which was separated by filtration and dried. The yield was 92%.

EXAMPLE 5

A mixture containing catechol (22 g), methallyl chloride (72 g) and a solvent (acetonitrile; 33 g) was fed over a catalyst (12 g) containing a mixture of phosphotungstic acid (1.5 g) and silicotungstic acid (0.5 g) on silica (10 g) at a rate of 5 ml per hr. The per pass conversion of catechol was 56% and selectivity to 7- benzofuranol, 97%. This product was mixed with benzene (solvent, 100 ml), methyl isocyanate (6.3 g) and triethyl amine catalyst (0.5 g) and refluxed for 2 hrs. The benzofuranol in the starting mixture got converted into carbofuran during refluxing. This was filtered and dried. The yield of carbofuran was 90%.

We claim:

1. An improved process for the preparation of carbofuran which comprises reacting catechol with beta methallyl halide or beta methallyl alcohol in the presence of a catalyst composite containing a heteropoly acid to obtain 7-hydroxy 2,3, dihydro 2,2, dimethyl benzofuran and reacting the 7-hydroxy 2,3, dihydro 2,2, dimethyl benzofuran with methyl isocyanate or with phosgene and methyl amine to obtain the carbofuran.

2. An improved process as claimed in claim 1 wherein the reaction of the catechol with the beta methallyl halide or methallyl alcohol is carried out at a temperature in the range of 100° to 400° C.

3. An improved process as claimed in claim 1 wherein the ratio of catechol with the methallyl halide or methallyl alcohol is in the range of 0.5 to 20 moles.

4. An improved process as claimed in claim 1 wherein the weight hourly velocity of the feed is in the range of 0.1 to 10 gm/gm.

5. An improved process as claimed in claim 1 wherein the heteropoly acid is selected from silicotungstic acid, phosphotungstic acid, silicomolybdic acid or mixtures thereof.

6. An improved process as claimed in claim 1 wherein the catalyst also contains a binder selected from silica, alumina, thoria, silica alumina, kieselguhr or clay.

7. An improved process as claimed in claim 6 wherein the catalyst is a solid composite consisting of the binder and the heteropoly acid, wherein the process occurs in the vapor phase.

8. An improved process as claimed in claim 6 wherein the concentration of the heteropoly acid in the catalyst composite is in the range of 5 to 80% by weight and the remaining being the binder.

9. An improved process as claimed in claim 6 wherein the beta methallyl halide used is selected from the chloride or bromide.

10. An improved process as claimed in claim 1 wherein the ratio of catechol with the methallyl halide or methallyl alcohol is in the range of around 10 moles.

11. An improved process as claimed in claim 1 wherein the weight hourly velocity of the feed is in the range of 0.3 to 2.0 gm/gm.

12. An improved process as claimed in claim 6 wherein the concentration of the heteropoly acid in the catalyst composite is in the range of between 10 to 30% by weight and the remaining being the binder.

* * * * *